US010993889B2

(12) United States Patent
Shimizu et al.

(10) Patent No.: US 10,993,889 B2
(45) Date of Patent: May 4, 2021

(54) POLYARYLETHERKETONE RESIN MATERIAL FOR DENTAL USE AND METHOD OF PRODUCING RESIN COMPOSITE MATERIAL FOR DENTAL USE

(71) Applicant: TOKUYAMA DENTAL CORPORATION, Tokyo (JP)

(72) Inventors: Tomonao Shimizu, Tokyo (JP); Junichiro Yamagawa, Tokyo (JP); Yuko Nagasawa, Tokyo (JP)

(73) Assignee: TOKUYAMA DENTAL CORPORATION

( * ) Notice: Subject to any disclaimer, the term of this patent is extended or adjusted under 35 U.S.C. 154(b) by 84 days.

(21) Appl. No.: 16/463,796

(22) PCT Filed: Nov. 28, 2017

(86) PCT No.: PCT/JP2017/042586
§ 371 (c)(1),
(2) Date: May 23, 2019

(87) PCT Pub. No.: WO2018/105443
PCT Pub. Date: Jun. 14, 2018

(65) Prior Publication Data
US 2019/0282455 A1    Sep. 19, 2019

(30) Foreign Application Priority Data

Dec. 9, 2016 (JP) .............................. JP2016-239401

(51) Int. Cl.
*A61K 6/891* (2020.01)
*A61C 5/77* (2017.01)
*A61C 13/20* (2006.01)
*A61C 13/087* (2006.01)
*C08L 71/10* (2006.01)
*A61K 6/17* (2020.01)
*A61K 6/76* (2020.01)
*A61K 6/78* (2020.01)
*C08L 81/02* (2006.01)

(52) U.S. Cl.
CPC .............. *A61K 6/891* (2020.01); *A61C 5/77* (2017.02); *A61C 13/087* (2013.01); *A61C 13/206* (2013.01); *A61K 6/17* (2020.01); *A61K 6/76* (2020.01); *A61K 6/78* (2020.01); *C08L 71/10* (2013.01); *C08L 81/02* (2013.01)

(58) Field of Classification Search
None
See application file for complete search history.

(56) References Cited

U.S. PATENT DOCUMENTS

| 2007/0197739 A1* | 8/2007 | Aneja ................. C08L 2666/20 |
| | | 525/437 |
| 2015/0306279 A1* | 10/2015 | El-Hibri .................. C08K 7/14 |
| | | 523/115 |
| 2017/0044348 A1* | 2/2017 | Yamagawa .............. C08K 3/36 |
| 2019/0282455 A1* | 9/2019 | Shimizu .................... A61C 5/77 |

FOREIGN PATENT DOCUMENTS

| JP | 2012-117189 A | 6/2012 | |
| JP | 2013-144778 A | 7/2013 | |
| JP | 2013-144784 A | 7/2013 | |
| JP | 2014-152150 A | 8/2014 | |
| JP | 2016-506263 A | 3/2016 | |
| JP | 2017-8028 A | 1/2017 | |
| WO | 2014-096058 A1 | 6/2014 | |
| WO | WO -2014096058 A1 * | 6/2014 | ............. A61L 27/18 |
| WO | WO-2015/170649 A1 | 11/2015 | |

OTHER PUBLICATIONS

Electronic and optical properties of boron nitride nanotubes, Oku et al., Journal of Physics and Chemistry of Solids, 69, (2008), 1228-1231 (Year: 2008).*
Ensinger [online], Aug. 16, 2016, [search date Feb. 1, 2018], internet: <URL:<https://web.archive.org/web/20160816232834/http://www.ensinger.jp/download/pdf/pdf_booklet/Medical_book.pdf>, in particular, pp. 10, 12, (medical plastic).
Seino, Hiroshi, et al., "Synthesis of Poly (Ether Ether Ketone) with Low Dielectric Property", Research Reports, National Institute of Technology, Fukushima College (2002), No. 43, pp. 25-29 (with English Abstract).
Braunam, S. K., et al., "Chemiluminescence studies of the thermooxidation of PEEK", Journal of Polymer Science: Part B:Polymer Physics, 1988, vol. 26, pp. 1205-1216 (in English).
Kisugi, Satoshi, et al., "Ultraviolet light resistance of PEEK-based composite dispersed with nanoparticles", Transactions of the Japan Society of Mechanical Engineers, 2010, vol. 76. No. 764, pp. 75-77 (with English Abstract).
Extended European Search Report for corresponding Application No. EP 17878737 dated Jun. 12, 2020 (6 pages).
Japanese Office Action for corresponding Application No. 2016-239401 dated Jun. 18, 2020 (15 pages) with English translation.
Wikipedia [online] "aromatic polyether ketone" Nov. 22, 2015. URL:https://web.archive.org/web/20151122012716/https://a.wikipedia.org/wikii%E8%8A%63%E9%A6%99%E6%97%8F%E3%83%9D%E3%83%AA%E3%82%A8%E3%83%BC%E3%83%86%E3%83%AB%E3%82%B1%E3%83%88%E3%83%B3 (3 pages), with English abstract.

* cited by examiner

*Primary Examiner* — Peter A Salamon
(74) *Attorney, Agent, or Firm* — Harness, Dickey & Pierce, P.L.C.

(57) ABSTRACT

A polyaryletherketone resin material is provided for dental use having high color tone stability in the case of exposure to visible light. The polyaryletherketone resin material for dental use includes a polyaryletherketone resin, which is a thermoplastic resin containing at least an aromatic group, an ether group (ether bond), and a ketone group (ketone bond) in its structural unit, and having a b* value of 10.0 or more in terms of colorimetric value of a 1.0 mm molded body in a CIELab color system under a black background condition.

7 Claims, No Drawings

POLYARYLETHERKETONE RESIN MATERIAL FOR DENTAL USE AND METHOD OF PRODUCING RESIN COMPOSITE MATERIAL FOR DENTAL USE

CROSS-REFERENCE TO RELATED APPLICATIONS

This application is a U.S. National Phase Application under 35 U.S.C. 371 of International Application No. PCT/JP2017/042586, filed on Nov. 28, 2017 and published in Japanese as WO 2018/105443 A1 on Jun. 14, 2018 which is based on and claims the benefit of priority from Japanese Patent Application No. 2016-239401 filed Dec. 9, 2016. The entire disclosures of all of the above applications are incorporated herein by reference.

BACKGROUND

Technical Field

The present invention relates to a polyaryletherketone resin material for dental use and a method of producing a resin composite material for dental use.

Related Art

Super engineering plastics are used in a wide range of applications in, for example, an electrical and electronic field, an aerospace field, an automotive industry, a medical field, and a general industrial field. Of the super engineering plastics, a polyaryletherketone resin is considered to be particularly promising for use in various fields by virtue of its excellent chemical properties and physical properties.

For example, in the field of dental treatment, there is a proposal of a technology involving using the polyaryletherketone resin as a dental material (for example, JP 2013-144778 A and JP 2013-144784 A). It is described that, for example, the polyaryletherketone resin is used in various dental applications, specifically a dental prosthesis, an artificial tooth, a dental plate, a dental implant (fixture, abutment, or superstructure), a dental crown restoration material, and an abutment construction material (JP 2013-144778 A).

In this connection, in dental treatment, resin-based materials other than the polyaryletherketone resin are also used in many situations, such as an artificial tooth, a dental prosthesis, dental crown restoration, abutment construction, and bonding. It is desired that those resin-based materials have imparted thereto physical properties regarding strength, aesthetics, and the like, in accordance with their respective applications. For example, color tone stability in the case of exposure to light, such as direct sunlight, is an important physical property in sustaining an aesthetic treatment effect for a long period of time.

It is desired that the polyaryletherketone resin material also have high color tone stability in order to sustain an aesthetic treatment effect over a long period of time, as with other resin-based materials. However, hitherto, there has been no finding on the color tone stability of the polyaryletherketone resin material.

The inventors of the present invention have made investigations on the color tone stability of a polyaryletherketone resin material in the case of exposure to light, and as a result, have found that the polyaryletherketone resin material is liable to undergo discoloration due to light, and hence has a problem with color tone stability in some cases.

Specifically, the inventors of the present invention have evaluated the color tone stability of the polyaryletherketone resin material at the time of exposure to light from a xenon lamp having inserted therein a UV filter on the basis of JIS T6003:2005, which specifies a test method for the color tone stability of a dental material, and as a result, have revealed that the polyaryletherketone resin material is significantly discolored as compared to other resin-based materials. The evaluation of the color tone stability of a dental material is generally performed by exposing a sample to light from a xenon lamp having inserted therein a UV filter or to direct sunlight. In the evaluation with light from a xenon lamp having inserted therein a UV filter, the state of the sample at the time of exposure mainly to visible light is evaluated. That is, it may be said that the polyaryletherketone resin material has poor color tone stability in the case of exposure to visible light.

In the case where the polyaryletherketone resin material is used in a dental application, when its color tone stability is poor, discoloration gradually occurs through exposure to light during use, and hence it is difficult to stably maintain high aesthetics for a long period of time.

In view of the foregoing, an object of the present invention is to provide a polyaryletherketone resin material for dental use having high color tone stability in the case of exposure to visible light (hereinafter sometimes referred to simply as color tone stability).

SUMMARY

The inventors of the present invention have made extensive investigations in order to achieve the above-mentioned object, and as a result, have found that high color tone stability can be imparted to a polyaryletherketone resin material by adjusting its b* value to 10.0 or more in terms of colorimetric value of a 1.0 mm molded body in a CIELab color system under a black background condition. Thus, the inventors have achieved the present invention.

That is, according to one embodiment of the present invention, there is provided a polyaryletherketone resin material for dental use, including a polyaryletherketone resin, and having a b* value of 10.0 or more in terms of colorimetric value of a 1.0 mm molded body in a CIELab color system under a black background condition.

The polyaryletherketone resin material for dental use according to the embodiment of the present invention preferably has an L* value of 60.0 or more in terms of colorimetric value of the 1.0 mm molded body in the CIELab color system under the black background condition.

The polyaryletherketone resin material for dental use according to the embodiment of the present invention preferably contains a filler, and the blending amount of the polyaryletherketone resin preferably falls within the range of from 40 mass % to 90 mass %.

Advantageous Effects of the Invention

According to the present invention, the polyaryletherketone resin material for dental use excellent in color tone stability can be provided. The polyaryletherketone resin material for dental use of the present invention is excellent in color tone stability, and hence can easily maintain its color tone immediately after treatment even when continuously used in any of various dental applications for a long period of time, thereby being able to maintain high aesthetics for a long period of time.

DETAILED DESCRIPTION OF THE EMBODIMENTS

A polyaryletherketone resin material for dental use of the present invention contains a polyaryletherketone resin.

The polyaryletherketone resin is a thermoplastic resin containing at least an aromatic group, an ether group (ether bond), and a ketone group (ketone bond) in its structural unit, and often has a linear polymer structure having phenylene groups bonded via an ether group and a ketone group. Typical examples of the polyaryletherketone resin include polyetherketone (PEK), polyetheretherketone (PEEK), polyetherketoneketone (PEKK), and polyetherketoneetherketoneketone (PEKEKK). The aromatic group constituting the structural unit of the polyaryletherketone resin may have a structure having two or more benzene rings like a biphenyl structure. In addition, the structural unit of the polyaryletherketone resin may contain a sulfonyl group or another monomer unit that is copolymerizable.

Of those polyaryletherketone resins, polyetheretherketone having a repeating unit in which ether groups and ketone groups constituting its main chain are arranged in the order "ether-ether-ketone", or polyetherketoneketone having a repeating unit in which the groups are arranged in the order "ether-ketone-ketone" is preferred from the viewpoints of a color tone and physical properties for use in dental applications.

The polyaryletherketone resin material for dental use of the present invention has a $b^*$ value of 10.0 or more in terms of colorimetric value of a 1.0 mm molded body in a CIELab color system under a black background condition.

The CIELab color system is a color system for representing the color tone of an object, and represents the color tone with an $L^*$ value representing lightness, an $a^*$ value representing red/green, and a $b^*$ value representing blue/yellow. The $L^*$ value is represented by a numerical value of from 0.0 to 90.0, and a larger numerical value means higher whiteness and a smaller numerical value means higher blackness. The $a^*$ value representing red/green represents green as a negative value and red as a positive value. The $b^*$ value representing blue/yellow represents blue as a negative value and yellow as a positive value, and a $b^*$ value of 10.0 or more indicates having yellowness at or higher than a certain level.

The reason why the polyaryletherketone resin material having a high $b^*$ value has high color tone stability is not necessarily clear, but the inventors of the present invention surmise the reason as described below.

When the polyaryletherketone resin is irradiated with visible light, such as direct sunlight, the polyaryletherketone resin absorbs the light, and its energy causes deterioration of the polyaryletherketone resin. It is surmised that, as a result of accumulation of such influence, the polyaryletherketone resin material exposed to visible light for a long period of time is changed in color tone as compared to that before the exposure to light. As described later, when the wavelength of the visible light to be radiated was changed, a large color tone change was shown in the case where purple light having a wavelength of from 380 nm to 450 nm was radiated. Accordingly, it is considered that the purple light, which has high energy among visible light beams, is absorbed by the polyaryletherketone resin, to thereby cause its discoloration, and it is surmised that the purple light makes a high contribution to the discoloration of the polyaryletherketone resin material. In this connection, the opposite color of purple ranges from yellowish green to yellow (yellowish colors), and hence, when the yellowness of the polyaryletherketone resin material is high such that the $b^*$ value of the polyaryletherketone resin material is 10.0 or more, the purple light is effectively absorbed by a yellow portion of the polyaryletherketone resin material. As a result, the amount of the purple light to be absorbed by the non-discolored polyaryletherketone resin itself is decreased, and hence the deterioration of the polyaryletherketone resin is suppressed. It is surmised that the discoloration of the polyaryletherketone resin material due to exposure to light is thus suppressed.

The $b^*$ value of the polyaryletherketone resin material for dental use of the present invention is measured with a colorimeter. Specifically, a sample plate having a thickness of 1.0 mm is brought into contact with a black background and irradiated with standard light C, and on the basis of reflected light obtained in this case, color tone data ($L^*$, $a^*$, $b^*$) in the CIELab color system including the $b^*$ value is obtained.

When the $b^*$ value of the polyaryletherketone resin material for dental use of the present invention is less than 10.0, the polyaryletherketone resin cannot be prevented from absorbing purple light responsible for discoloration. Accordingly, the polyaryletherketone resin is deteriorated, and hence the color tone stability of the polyaryletherketone resin material for dental use of the present invention becomes poor. In order to suppress the absorption of purple light by the polyaryletherketone resin to achieve more excellent color tone stability of the polyaryletherketone resin material for dental use of the present invention, the $b^*$ value is preferably 15.0 or more, more preferably 18.0 or more, still more preferably 20.0 or more, most preferably 25.0 or more. Meanwhile, in view of an aesthetic requirement for use in dental applications, the $b^*$ value is preferably 30.0 or less, preferably 28.0 or less.

A method of adjusting the $b^*$ value of the polyaryletherketone resin material for dental use of the present invention to 10.0 or more is not particularly limited, and examples thereof may include: a method involving compositing a yellowish substance, such as a dye, pigment, or resin exhibiting a yellowish color, and the polyaryletherketone resin; and a method involving applying a coating of the yellowish substance to the surface of the polyaryletherketone resin material for dental use. An example of the yellowish substance is a substance having a maximum absorption wavelength in the range of from 360 nm to 560 nm in the measurement range of from 360 nm to 830 nm. Of the above-mentioned methods of adjusting the $b^*$ value of the polyaryletherketone resin material for dental use of the present invention to 10.0 or more, it is preferred that the polyaryletherketone resin material for dental use having a $b^*$ value of 10.0 or more be obtained by compositing the yellowish substance and the polyaryletherketone resin because of the ease with which a stable color tone is exhibited for a long period of time and a $b^*$ value of 10.0 or more is imparted. In addition, the compositing of the polyaryletherketone resin and another material, such as the yellowish substance, is performed at a temperature equal to or higher than the melting point of the polyaryletherketone resin, i.e., 340° C., and hence the yellowish substance is preferably an inorganic pigment exhibiting a yellowish color that has high thermal stability.

The inorganic pigment exhibiting a yellowish color may be used without any particular limitation as long as the $b^*$ value of the polyaryletherketone resin material can be adjusted to 10.0 or more, and a yellow, yellowish green, brown, or orange pigment may be used. Of those pigments, a yellow or brown inorganic pigment is preferably used because an appropriate color for dental applications can be easily imparted to the polyaryletherketone resin material.

The yellow inorganic pigment may be exemplified by an inorganic pigment having a maximum absorption wavelength in the range of from 360 nm to 490 nm in the measurement range of from 360 nm to 830 nm, and examples thereof include Pigment Yellow 24 (Cr—Ti—Sb composite oxide), Pigment Yellow 42 (iron yellow), Pigment Yellow 53 (Ti—Ni—Sb composite oxide, titanium nickel antimony yellow), Pigment Yellow 157 (Ti—Ni—Ba composite oxide, titanium nickel barium yellow), Pigment Yellow 158 (Sn—V composite oxide, Sn—Ti—V composite oxide, vanadium tin yellow), Pigment Yellow 159 (Pr—Zr—Si composite oxide, praseodymium yellow), Pigment Yellow 160 (Zr—V composite oxide, Zr—V—In composite oxide, Zr—Ti—V—In composite oxide, vanadium zirconium yellow), Pigment Yellow 162 (Ti—Cr—Nb composite oxide, titanium chromium niobium yellow), Pigment Yellow 163 (Cr—Ti—W composite oxide, chromium titanium tungsten yellow), Pigment Yellow 184 (bismuth vanadate), Pigment Brown 24 (Cr—Ti—Sb composite oxide, chromium titanium antimony yellow), and a Ti—W—Fe composite oxide (titanium tungsten iron yellow).

In addition, the brown inorganic pigment may be exemplified by an inorganic pigment having a maximum absorption wavelength in the range of from 490 nm to 560 nm in the measurement range of from 360 nm to 830 nm, and examples thereof include Pigment Yellow 119 (Fe—Zn composite oxide, Fe—Zn—Ti composite oxide, zinc iron brown), Pigment Brown 6 (iron oxide brown), Pigment Brown 8 (manganese oxide), Pigment Brown 29 (Cr—Fe composite oxide, chromium iron brown), Pigment Brown 33 (Zn—Cr—Fe composite oxide, Zn—Al—Cr—Fe composite oxide, zinc iron chromium brown), and Pigment Brown 48 (Fe—Al—Ti composite oxide, alumina titania iron brown).

Of those inorganic pigments, an inorganic pigment formed of a composite oxide pigment is preferably used because its use makes it easy to stably perform the compositing of the inorganic pigment and the polyaryletherketone resin. As described above, when the inorganic pigment and the polyaryletherketone resin are composited, the compositing is generally performed by kneading the polyaryletherketone resin and the inorganic pigment melted by being heated to a temperature equal to or higher than the melting point of the polyaryletherketone resin material. As the polyaryletherketone resin has a melting point at a high temperature of from about 340° C. to about 390° C., the pigment is also exposed to high temperature during the kneading, and hence a composite oxide pigment having higher thermal stability is preferably used. Herein, the composite oxide pigment refers to a pigment formed of a solid solution of a plurality of metal oxides, and has a structure obtained by substituting a metal atom in a single oxide structure with other atoms, such as second and third atoms.

Examples of the inorganic pigment formed of a yellow composite oxide pigment as described above include inorganic pigments each having a maximum absorption wavelength in the range of from 360 nm to 490 nm in the measurement range of from 360 nm to 830 nm, such as Pigment Yellow 24 (Cr—Ti—Sb composite oxide), Pigment Yellow 53 (Ti—Ni—Sb composite oxide, titanium nickel antimony yellow), Pigment Yellow 157 (Ti—Ni—Ba composite oxide, titanium nickel barium yellow), Pigment Yellow 158 (Sn—V composite oxide, Sn—Ti—V composite oxide, vanadium tin yellow), Pigment Yellow 159 (Pr—Zr—Si composite oxide, praseodymium yellow), Pigment Yellow 160 (Zr—V composite oxide, Zr—V—In composite oxide, Zr—Ti—V—In composite oxide, vanadium zirconium yellow), Pigment Yellow 162 (Ti—Cr—Nb composite oxide, titanium chromium niobium yellow), Pigment Yellow 163 (Cr—Ti—W composite oxide, chromium titanium tungsten yellow), Pigment Brown 24 (Cr—Ti—Sb composite oxide, chromium titanium antimony yellow), and a Ti—W—Fe composite oxide (titanium tungsten iron yellow).

Examples of the inorganic pigment formed of a brown composite oxide pigment include inorganic pigments each having a maximum absorption wavelength in the range of from 490 nm to 560 nm in the measurement range of from 360 nm to 830 nm, such as Pigment Yellow 119 (Fe—Zn composite oxide, Fe—Zn—Ti composite oxide, zinc iron brown), Pigment Brown 29 (Cr—Fe composite oxide, chromium iron brown), Pigment Brown 33 (Zn—Cr—Fe composite oxide, Zn—Al—Cr—Fe composite oxide, zinc iron chromium brown), and Pigment Brown 48 (Fe—Al—Ti composite oxide, alumina titania iron brown).

In addition, in order that color unevenness may be less liable to occur at the time of the kneading/molding of the polyaryletherketone resin material, it is preferred to use, as the inorganic pigment exhibiting a yellowish color, an inorganic pigment containing any one of the following elements: aluminum, zinc, tungsten, iron, titanium, bismuth, vanadium, and praseodymium, it is more preferred to use an inorganic pigment formed of a composite oxide including oxides of at least two or more kinds of metal elements selected from the group consisting of aluminum, zinc, tungsten, iron, titanium, bismuth, vanadium, and praseodymium, and it is still more preferred to use an inorganic pigment formed of a composite oxide including oxides of any one element selected from the group consisting of aluminum, zinc, tungsten, titanium, bismuth, vanadium, and praseodymium, and of iron. The reason why the use of any such inorganic pigment makes color unevenness less liable to occur is not clear, but it is surmised that the inorganic pigment has an improved affinity at the time of dispersion in the polyaryletherketone resin by virtue of containing the above-mentioned elements.

Of such inorganic pigments each formed of a composite oxide including oxides of any one element selected from the group consisting of aluminum, zinc, tungsten, titanium, bismuth, vanadium, and praseodymium, and of iron, a compound represented by the following compositional formula (I) is preferred from the viewpoints of a coloring property, aesthetics, and color unevenness:

$$Al_xFe_{2-x}TiO_5 \cdot ZTiO_2 \qquad (I)$$

where x and Z fall within the ranges of 0<x<2 and 0≤Z.

An example of the composite oxide pigment represented by the compositional formula (I) may be Pigment Brown 48 (Fe—Al—Ti composite oxide, alumina titania iron brown). The color arrangement of the pigment may be finely adjusted by adjusting ratios at which the titanium atom of titanium dioxide is substituted with aluminum and iron.

The blending ratio of the inorganic pigment in the polyaryletherketone resin material for dental use only needs to be appropriately adjusted so that the b* value may be 10.0 or more. From the viewpoint of efficiently obtaining a color tone stability-enhancing effect, the blending ratio is preferably 0.05 part by mass or more, more preferably 0.1 part by mass or more, still more preferably 0.3 part by mass or more in 100 parts by mass of the polyaryletherketone resin material for dental use. In addition, from the viewpoint of an influence on the strength of the polyaryletherketone resin material for dental use, the blending ratio is preferably 15 parts by mass or less, more preferably 10 parts by mass or less, still more preferably 8 parts by mass or less.

The particle diameter of the pigment is not particularly limited, but its volume-average particle diameter measured by a laser scattering method (LS230 manufactured by Beckman Coulter, Inc., using ethanol as a dispersion medium) is preferably from 0.01 µm to 10 µm, more preferably from 0.05 µm to 3 µm, most preferably from 0.1 µm to 1 µm. When having a fine particle diameter, the pigment has enhanced dispersibility, and hence can provide high coloring by being mixed in a smaller amount. However, when the particle diameter is excessively small, it becomes difficult to disintegrate aggregation, resulting in an increased risk of a degradation in dispersibility.

In addition, the inorganic pigment may be subjected to surface treatment with a surface treatment agent or the like for the purpose of, for example, modifying its surface properties to improve its affinity for the polyaryletherketone resin and other components.

The polyaryletherketone resin material for dental use contains the polyaryletherketone resin as described above, and may consist only of the polyaryletherketone resin, but may be a blend of the polyaryletherketone resin and another resin.

The other resin that may be blended with the polyaryletherketone resin is not particularly limited, but is preferably a resin that does not significantly degrade the physical properties of the polyaryletherketone resin, such as rigidity and toughness. Examples thereof include a polyarylate resin, a polycarbonate resin, a polyethylene terephthalate resin, a polyphthalamide resin, a polytetrafluoroethylene resin, and a polyphenylene ether resin. When the polyaryletherketone resin and the other resin are blended, the ratio of the polyaryletherketone resin in all the resins is preferably 50 mass % or more, more preferably 70 mass % or more, still more preferably 90 mass % or more, still more preferably 99 mass % or more.

The polyaryletherketone resin material for dental use of the present invention may have blended therein inorganic functional particles, such as an inorganic pigment other than the above-mentioned inorganic pigment exhibiting a yellowish color, an inorganic filler, an antistatic agent, an X-ray contrast medium, a UV absorbing material, and a fluorescent agent. Both of the above-mentioned inorganic pigment exhibiting a yellowish color and the inorganic functional particles are sometimes collectively referred to as "inorganic particles".

The inorganic filler is preferably blended because its blending makes it easy to impart, to the polyaryletherketone resin material, appropriate physical properties for dental applications (e.g., mechanical physical properties, such as strength, aesthetics-related physical properties, such as glossiness, and processability, such as machining processability). As the inorganic filler, a known one may be utilized without any particular limitation. Examples of materials for the filler include: silica glass, borosilicate glass, soda glass, aluminosilicate glass, and fluoroaluminosilicate glass, and glass containing a heavy metal (e.g., barium, strontium, or zirconium); glass ceramics, such as crystallized glass obtained by precipitating a crystal in any such glass, and a crystallized glass obtained by precipitating a crystal such as diopside or leucite; composite inorganic oxides, such as silica-zirconia, silica-titania, and silica-alumina; oxides obtained by adding Group I metal oxides to those composite inorganic oxides; and metal inorganic oxides, such as silica, alumina, titania, and zirconia. From the viewpoints of being less harmful to a living body when blended, and enhancing whiteness, thereby being aesthetically advantageous, the inorganic filler is suitably a composite inorganic oxide, an oxide obtained by adding a Group I metal oxide to a composite inorganic oxide, or a metal oxide, particularly suitably silica-based particles each formed of silica or a composite oxide of the silica and another metal oxide, or titanium dioxide-based particles each formed of titania or a composite oxide of the titania and another metal oxide. Those inorganic fillers may be used alone or as a mixture thereof. The particle diameter of the inorganic filler is not particularly limited, but falls within preferably the range of from 0.05 µm to 5 µm, more preferably the range of from 0.1 µm to 3 µm. The inorganic filler may have its surface subjected to surface treatment with a surface treatment agent, such as a silane coupling agent, before use. The blending amount of the inorganic filler falls within preferably the range of from 10 parts by mass to 70 parts by mass, more preferably the range of from 15 parts by mass to 60 parts by mass, still more preferably the range of from 20 parts by mass to 50 parts by mass with respect to 100 parts by mass of the polyaryletherketone resin material. When the blending amount of the inorganic filler is set to 10 parts by mass or more, physical properties, such as mechanical characteristics, appropriate for dental applications can be easily obtained. In addition, when the blending amount is set to 70 parts by mass or less, during the melt-kneading of the polyaryletherketone resin and the inorganic filler, an increase in viscosity is suppressed to facilitate handling, and also facilitate the enhancement of the dispersibility of particle components.

The blending amount of those inorganic particles including the inorganic pigment exhibiting a yellowish color and the inorganic filler only needs to be appropriately decided in consideration of required physical properties, such as the color tone including the b* value, strength, and toughness. From the viewpoint that appropriate physical properties as a dental material can be easily obtained, the blending amount falls within preferably the range of from 10 parts by mass to 70 parts by mass, more preferably the range of from 15 parts by mass to 60 parts by mass, still more preferably the range of from 20 parts by mass to 50 parts by mass with respect to 100 parts by mass of the polyaryletherketone resin material. When the blending amount of the inorganic particles is set to 10 parts by mass or more, physical properties, such as mechanical characteristics, appropriate for dental applications can be easily obtained. In addition, when the blending amount is set to 70 parts by mass or less, during the melt-kneading of the polyaryletherketone resin and the inorganic particles, an increase in viscosity is suppressed to facilitate handling, and also facilitate the enhancement of the dispersibility of particle components.

When the polyaryletherketone resin material for dental use of the present invention is irradiated with purple light, the polyaryletherketone resin is discolored. Therefore, a large blending amount of the polyaryletherketone resin, which increases the degree of the discoloration and leads to poor color tone stability, is preferred because the color tone stability-improving effect based on the adjustment of the b* value to 10.0 or more is remarkably exhibited. For this reason, the blending amount of the polyaryletherketone resin in the polyaryletherketone resin material for dental use is preferably 40 parts by mass or more, more preferably 50 parts by mass or more, still more preferably 55 parts by mass or more with respect to 100 parts by mass of the polyaryletherketone resin material for dental use. In addition, from the viewpoints of physical properties for use in dental applications, the blending amount of the polyaryletherketone resin in the polyaryletherketone resin material for dental use is preferably 90 parts by mass or less, more preferably 85 parts by mass or less, still more preferably 80 parts by mass or less with respect to 100 parts by mass of the polyaryletherketone resin material for dental use.

With regard to the color tone of the polyaryletherketone resin material for dental use of the present invention, its L* value and a* value are not particularly limited as long as the b* value is 10.0 or more. However, as whiteness increases, discoloration due to light becomes more liable to be conspicuous, and hence the effect of the present invention based on the adjustment of the b* value to 10.0 or more is more remarkably exhibited. For this reason, the L* value is preferably 60.0 or more, preferably 65.0 or more, still more preferably 70.0 or more, most preferably 75.0 or more. From the viewpoint of aesthetic restoration, the L* value falls within preferably the range of from 65.0 to 85.0, more preferably the range of from 70.0 to 80.0. In addition, the a* value is not particularly limited, but when the polyaryletherketone resin material for dental use of the present invention is used in a dental crown restoration application, from the viewpoint of aesthetics, the a* value falls within preferably the range of from −2.0 to 6.0, more preferably the range of from −1.0 to 4.0.

A method of producing the polyaryletherketone resin material for dental use of the present invention is not particularly limited, but in the case of a polyaryletherketone resin composite material obtained by compositing the polyaryletherketone resin and the inorganic particles, such as the inorganic pigment or the inorganic filler, the polyaryletherketone resin composite material is generally produced through a melt-kneading step including melting the polyaryletherketone resin and the inorganic particles by heating at a temperature equal to or higher than the melting point of the polyaryletherketone resin, for example, from 340° C. to 500° C., preferably from 350° C. to 450° C., and kneading the polyaryletherketone resin and the inorganic particles. A known technique may be used as a technique for performing the melt-kneading without any particular limitation, and for example, melt-kneading with a mixer with a heating device or melt-kneading with an extruder (e.g., a single-screw melt-kneading apparatus, a twin-screw melt-kneading apparatus, a triple-screw melt-kneading apparatus, or a quadruple-screw melt-kneading apparatus) may be performed. Of those, melt-kneading with an extruder, which is capable of continuous production and can easily provide a composite material having a particle shape (pellet shape) that is easy to handle in the next step as described later, is preferred, and melt-kneading with a twin-screw melt-kneading apparatus is most preferred.

After the melt-kneading step, various post-processes may be performed as required. For example, the melt-kneaded product in a high-temperature state immediately after the melt-kneading step may be directly molded into a desired shape by injection molding, extrusion molding, or the like. In addition, the melt-kneaded product in a high-temperature state immediately after the melt-kneading step may be first molded into a member to be secondarily processed having a pellet shape, a powder shape, a block shape, or the like, and then the member to be secondarily processed may be used and molded into a desired shape by further performing any of various types of processing, such as injection molding, extrusion molding, laser forming, cutting processing, machining processing, and polishing processing. The shape of the member to be secondarily processed is preferably a pellet shape (in particular, a cylindrical shape having a diameter of from about 0.5 mm to about 5 mm and a length of about 1 mm to about 10 mm) from the viewpoint of the ease of handling. The composite material having a pellet shape can be easily obtained by cutting a composite material, which has been extruded into a strand shape from an extruder (e.g., a single-screw melt-kneading apparatus, a twin-screw melt-kneading apparatus, a triple-screw melt-kneading apparatus, or a quadruple-screw melt-kneading apparatus), at desired intervals. The member to be secondarily processed that has been obtained in a pellet shape may, for example: be directly molded into a desired shape for use as a dental member by injection molding, extrusion molding, hot-press molding, or the like; or be first molded into a block shape or a disc shape by injection molding, extrusion molding, hot-press molding, or the like, followed by machining processing of the resultant into a desired shape for use as a dental member. Further, the member obtained by directly molding the melt-kneaded product into a desired shape, the member to be secondarily processed itself, or a product obtained by molding the member to be secondarily processed into a desired shape may be subjected to a heat treatment step in order to relax a stress generated at the time of molding to achieve excellent strength. The heat treatment step may be performed at a temperature equal to or higher than the glass transition temperature of the polyaryletherketone resin and lower than its melting point.

The polyaryletherketone resin material for dental use of the present invention may be utilized in various dental applications, such as a dental prosthesis, an artificial tooth, a dental plate, a dental implant, a dental crown restoration material, and an abutment construction material, and is preferably used in a dental crown restoration application in which high color tone stability and aesthetics are required.

EXAMPLES

The present invention is specifically described below by way of Examples. However, the present invention is not limited thereto. Abbreviations and names shown in Examples are as described below.
Polyaryletherketone Resin
PEEK: polyetheretherketone resin (manufactured by Daicel-Evonik Ltd.: VESTAKEEP2000G)
Yellowish Inorganic Pigment
Yellow Inorganic Pigment
Y: Ti—W—Fe composite oxide (titanium tungsten iron yellow; manufactured by Tokan Material Technology Co., Ltd., 42-543A)
Y184: Pigment Yellow 184 (bismuth vanadate)
(Brown Inorganic Pigment)
Y119: Pigment Yellow 119 (Fe—Zn—Ti composite oxide, zinc iron brown)
B48: Pigment Brown 48 (Fe—Al—Ti composite oxide, alumina titania iron brown)
All of the pigments used have a volume-average particle diameter of 500 nm.
[Inorganic Filler]
F1: $SiO_2$ (spherical shape, volume-average particle diameter: 1 μm, γ-methacryloyloxypropyltrimethoxysilane surface treatment product)
F2: $TiO_2$ (spherical shape, volume-average particle diameter: 0.25 μm)
Test methods are as described below.
(Melt-Kneading of Polyaryletherketone Resin and Inorganic Particles)
Predetermined amounts of the polyaryletherketone resin and the inorganic particles were loaded into a twin-screw melt-kneading apparatus, and were melt-kneaded under the conditions of a barrel temperature of 360° C. and a number of rotations of 500 rpm to provide a polyaryletherketone resin composite material. A strand discharged from a nozzle was cooled in a water bath, and then a pelletizer was used to provide pellets each having a cylindrical shape having a diameter of from about 1 mm to about 3 mm and a length of from about 2 mm to about 4 mm.

(Measurement of Color Tone and Evaluation of Color Tone Stability)

The pellets of the polyaryletherketone resin material were molded with a hot-press machine into a size of 20 mm×20 mm×t1 mm to serve as a test piece (having a light irradiation surface measuring 20 mm×20 mm). With the use of a colorimeter (manufactured by Tokyo Denshoku Co., Ltd.: TC-1800MKII), first, the test piece was irradiated with standard light C under a black background, and on the basis of reflected light obtained in this case, color tone data ($L^*_1$, $a^*_1$, $b^*_1$) on the test piece before exposure to light in a CIELab color system was obtained. In the color tone data on the test piece before exposure to light, average values of ($L^*_1$, $a^*_1$, $b^*_1$) for five test pieces serve as the color tone of the polyaryletherketone resin material.

The test piece was placed in water kept at 37° C. so that the irradiation surface of the test piece was at a depth of 10 mm from the surface of the water. A xenon lamp having inserted therein a UV filter was placed so that an illuminance at the irradiation surface of the test piece was 150,000 lux, and the test piece was irradiated with light for 2 days. After that, on the basis of reflected light obtained in the case of irradiation with standard light C under a black background, color tone data ($L^*_2$, $a^*_2$, $b^*_2$) on the test piece after exposure to light in the CIELab color system was obtained. On the basis of the obtained data, a color difference $\Delta E^*$ between before exposure to light and after exposure was calculated. The test was performed for five test pieces, and the average value of $\Delta E^*$ was determined. $\Delta E^*$ is calculable in accordance with the following equation (1), and it may be said that, as its value becomes smaller, a color tone change due to exposure to light becomes smaller, that is, color tone stability becomes higher.

$$\Delta E^* = ((L^*_1 - L^*_2)^2 + (a^*_1 - a^*_2)^2 + (b^*_1 - b^*_2)^2)^{1/2} \quad (1)$$

Example 1

120 g of PEEK, 63.8 g of the inorganic filler F1, 16 g of the inorganic filler F2, and 0.2 g of the yellowish inorganic pigment Y were melt-kneaded using a twin-screw melt-kneading apparatus at a barrel temperature of 360° C., and a sample discharged in a strand shape was cut with a pelletizer to provide pellets of a polyaryletherketone resin material. The pellets were molded into a size of 20 mm×20 mm×t1 mm using a hot-press machine.

The molded body was irradiated with standard light C under a black background using a colorimeter (manufactured by Tokyo Denshoku Co., Ltd.: TC-1800MKII), and on the basis of reflected light obtained in this case, color tone data ($L^*$, $a^*$, $b^*$) was obtained. Then, the color tone stability of the molded body was evaluated, and $\Delta E^*$ was determined.

The composition of the polyaryletherketone resin material is shown in Table 1, and the evaluation results of the color tone and the color tone stability are shown in Table 2.

Examples 2 to 36 and Comparative Examples 1 to 10

Polyaryletherketone resin materials were each obtained in accordance with Example 1 except that the composition of the polyaryletherketone resin material was changed as shown in Table 1, and the color tone and color tone stability of each of the polyaryletherketone resin materials were evaluated. The evaluation results of the color tone and the color tone stability are shown in Table 2.

In these Examples, factors greatly influencing the color tone were the inorganic filler F2 and the inorganic pigment. In view of this, a product having blended therein no inorganic pigment was defined as a base composition, and when the inorganic pigment was blended, color tone adjustment was performed by reducing the amount of the inorganic filler F1 in the base composition by the same amount as the blending amount of the inorganic pigment. In addition, the adjustment of the blending ratio of the polyaryletherketone resin in the case where the amount of the polyaryletherketone resin was increased or reduced was performed by reducing or increasing the amount of the inorganic filler F1 by the same amount.

TABLE 1

| | Polyaryletherketone resin material [part(s) by mass] | | | | | | |
|---|---|---|---|---|---|---|---|
| | Polyaryletherketone resin | Inorganic particles | | | | | |
| | | Inorganic filler | | Inorganic pigment exhibiting yellowish color | | | |
| | PEEK | F1 | F2 | Y | Y119 | Y184 | B48 |
| Example 1 | 60 | 31.9 | 8 | 0.1 | — | — | — |
| Example 2 | 60 | 31.4 | 8 | 0.6 | — | — | — |
| Example 3 | 60 | 31 | 8 | 1 | — | — | — |
| Example 4 | 60 | 30.5 | 8 | 1.5 | — | — | — |
| Example 5 | 60 | 29 | 8 | 3 | — | — | — |
| Example 6 | 60 | 26 | 8 | 6 | — | — | — |
| Example 7 | 60 | 31.9 | 8 | — | 0.1 | — | — |
| Example 8 | 60 | 31.4 | 8 | — | 0.6 | — | — |
| Example 9 | 60 | 31 | 8 | — | 1 | — | — |
| Example 10 | 60 | 30.5 | 8 | — | 1.5 | — | — |
| Example 11 | 60 | 29 | 8 | — | 3 | — | — |
| Example 12 | 60 | 26 | 8 | — | 6 | — | — |
| Example 13 | 60 | 31.9 | 8 | — | — | 0.1 | — |
| Example 14 | 60 | 31.4 | 8 | — | — | 0.6 | — |
| Example 15 | 60 | 31 | 8 | — | — | 1 | — |
| Example 16 | 60 | 30.5 | 8 | — | — | 1.5 | — |
| Example 17 | 60 | 29 | 8 | — | — | 3 | — |
| Example 18 | 60 | 26 | 8 | — | — | 6 | — |

TABLE 1-continued

| | Polyaryletherketone resin material [part(s) by mass] | | | | | | |
|---|---|---|---|---|---|---|---|
| | Polyaryletherketone resin | Inorganic particles | | | | | |
| | | Inorganic filler | | Inorganic pigment exhibiting yellowish color | | | |
| | PEEK | F1 | F2 | Y | Y119 | Y184 | B48 |
| Example 19 | 60 | 31.95 | 8 | — | — | — | 0.05 |
| Example 20 | 60 | 31.9 | 8 | — | — | — | 0.1 |
| Example 21 | 60 | 31.7 | 8 | — | — | — | 0.3 |
| Example 22 | 60 | 31.4 | 8 | — | — | — | 0.6 |
| Example 23 | 60 | 31 | 8 | — | — | — | 1 |
| Example 24 | 60 | 30.5 | 8 | — | — | — | 1.5 |
| Example 25 | 60 | 29 | 8 | — | — | — | 3 |
| Example 26 | 60 | 26 | 8 | — | — | — | 6 |
| Example 27 | 60 | 35.8 | 3 | 1.2 | — | — | — |
| Example 28 | 60 | 22 | 15 | 3 | — | — | — |
| Example 29 | 60 | 35.8 | 3 | — | — | — | 1.2 |
| Example 30 | 60 | 22 | 15 | — | — | — | 3 |
| Example 31 | 80 | 6 | 8 | 6 | — | — | — |
| Example 32 | 50 | 36 | 8 | 6 | — | — | — |
| Example 33 | 80 | 6 | 8 | — | — | — | 6 |
| Example 34 | 50 | 36 | 8 | — | — | — | 6 |
| Example 35 | 60 | 39 | — | 1 | — | — | — |
| Example 36 | 60 | 39 | — | — | — | — | 1 |
| Comparative Example 1 | 60 | 32 | 8 | — | — | — | — |
| Comparative Example 2 | 60 | 31.99 | 8 | 0.01 | — | — | — |
| Comparative Example 3 | 60 | 31.99 | 8 | — | 0.01 | — | — |
| Comparative Example 4 | 60 | 31.99 | 8 | — | — | 0.01 | — |
| Comparative Example 5 | 60 | 31.99 | 8 | — | — | — | 0.01 |
| Comparative Example 6 | 60 | 37 | 3 | — | — | — | — |
| Comparative Example 7 | 60 | 25 | 15 | — | — | — | — |
| Comparative Example 8 | 80 | 12 | 8 | — | — | — | — |
| Comparative Example 9 | 50 | 42 | 8 | — | — | — | — |
| Comparative Example 10 | 60 | 40 | — | — | — | — | — |

TABLE 2

| | Color tone | | | Color tone stability ΔE* |
|---|---|---|---|---|
| | L* | a* | b* | |
| Example 1 | 82.9 | 0.9 | 10.8 | 5.0 |
| Example 2 | 80.6 | 1.6 | 15.4 | 4.2 |
| Example 3 | 79.7 | 2.4 | 18.8 | 3.9 |
| Example 4 | 78.1 | 2.8 | 20.7 | 3.3 |
| Example 5 | 72.9 | 4.0 | 24.3 | 3.1 |
| Example 6 | 68.5 | 6.1 | 27.7 | 2.1 |
| Example 7 | 82.1 | 2.1 | 10.2 | 4.8 |
| Example 8 | 80.1 | 2.7 | 13.9 | 4.6 |
| Example 9 | 79.4 | 3.3 | 16.7 | 4.1 |
| Example 10 | 77.5 | 3.7 | 19.5 | 3.7 |
| Example 11 | 70.9 | 4.7 | 22.0 | 3.2 |
| Example 12 | 66.7 | 6.9 | 24.8 | 2.8 |
| Example 13 | 83.1 | −0.1 | 12.4 | 4.8 |
| Example 14 | 81.1 | −0.3 | 17.5 | 4.0 |
| Example 15 | 89.4 | 0.1 | 20.4 | 3.3 |
| Example 16 | 78.1 | 0.3 | 22.6 | 2.9 |
| Example 17 | 73.4 | −0.2 | 26.6 | 2.4 |
| Example 18 | 69.2 | 0.1 | 29.7 | 2.2 |
| Example 19 | 83.6 | 0.7 | 10.8 | 4.9 |
| Example 20 | 83.1 | 1.1 | 11.0 | 4.9 |
| Example 21 | 82.3 | 1.3 | 12.4 | 4.8 |
| Example 22 | 81.0 | 1.8 | 15.1 | 4.3 |
| Example 23 | 79.8 | 2.2 | 18.3 | 3.7 |
| Example 24 | 78.3 | 2.7 | 21.1 | 3.3 |
| Example 25 | 73.6 | 4.5 | 24.4 | 3.0 |
| Example 26 | 68.3 | 6.0 | 27.5 | 2.2 |
| Example 27 | 74.1 | 2.5 | 20.5 | 3.4 |
| Example 28 | 82.6 | 2.1 | 20.6 | 3.4 |
| Example 29 | 73.7 | 2.5 | 20.7 | 3.5 |
| Example 30 | 82.2 | 2.2 | 21.0 | 3.3 |
| Example 31 | 68.1 | 5.8 | 27.5 | 2.2 |
| Example 32 | 68.6 | 6.0 | 27.1 | 2.3 |
| Example 33 | 68.3 | 6.4 | 26.9 | 2.4 |
| Example 34 | 68.0 | 6.1 | 27.9 | 2.3 |
| Example 35 | 67.6 | 2.1 | 21.0 | 3.3 |
| Example 36 | 67.1 | 2.0 | 21.6 | 3.3 |
| Comparative Example 1 | 84.5 | −0.2 | 8.7 | 5.6 |
| Comparative Example 2 | 83.7 | 0.5 | 9.1 | 5.2 |
| Comparative Example 3 | 83.7 | 0.5 | 9.0 | 5.2 |
| Comparative Example 4 | 83.7 | 0.0 | 9.8 | 5.3 |
| Comparative Example 5 | 83.7 | 0.5 | 9.4 | 5.2 |
| Comparative Example 6 | 78.4 | 0.0 | 8.7 | 5.3 |
| Comparative Example 7 | 86.6 | −0.3 | 8.4 | 5.9 |
| Comparative Example 8 | 82.6 | 0.0 | 8.5 | 6.2 |
| Comparative Example 9 | 84.7 | 0.1 | 8.9 | 5.3 |
| Comparative Example 10 | 72.2 | 0.1 | 8.8 | 5.2 |

As apparent from the evaluation results, Examples 1 to 36 each having a b* value of 10.0 or more in terms of colorimetric value of a 1.0 mm molded body in the CIELab color system under a black background condition showed high color tone stability as compared to Comparative Examples 1 to 10 each having a b* value of less than 10.0. In addition, all of the polyaryletherketone resin materials each having a b* value of 15.0 or more showed high color tone stability as compared to the polyaryletherketone resin materials each having a b* value of less than 15.0. All of the polyaryletherketone resin materials each having a b* value of 18.0 or more showed high color tone stability as compared to the polyaryletherketone resin materials each having a b* value of less than 18.0. All of the polyaryletherketone resin materials each having a b* value of 20.0 or more showed high color tone stability as compared to the polyaryletherketone resin materials each having a b* value of less than 20.0. All of the polyaryletherketone resin materials each having a b* value of 25.0 or more showed high color tone stability as compared to the polyaryletherketone resin materials each having a b* value of less than 25.0.

Examples 4, 27, 28, and 35 (in which the blending amount of F2 was changed without changes in blending ratios of the polyaryletherketone resin and the inorganic particles, and the b* values were adjusted to be 10.0 or more and nearly equal to each other by the blending of the inorganic pigment Y exhibiting a yellowish color) show nearly equal b* values, and also have comparably high degrees of color tone stability, but differ from each other in L* value, which increases in the order of Example 35, Example 27, Example 4, and Example 28 (in order from the smallest blending amount of F2). Comparative Examples 1, 6, 7, and 10 corresponding to those Examples (having blended therein no inorganic pigment exhibiting a yellowish color) have b* values of less than 10.0, have L* values increasing in the order of Comparative Examples 10, 6, 1, and 7 (in order from the smallest blending amount of F2), and have poorer color tone stability in the same order. This means that, when the b* value is less than 10.0, a higher L* value leads to poorer color tone stability, and when the b* value is 10.0 or more, the color tone stability is comparably high irrespective of the L* value, suggesting that, as the L* value increases, the color tone stability-enhancing effect obtained by adjusting the b* value to 10.0 or more increases. The same applies to Examples 24, 29, 30, and 35, in which the kind of the inorganic pigment exhibiting a yellowish color was changed.

Examples 6, 31, and 32 (in which the blending ratios of the polyaryletherketone resin and the inorganic particles were changed while the blending amount of F2 was kept constant, and the b* values were adjusted to be 10.0 or more and nearly equal to each other by the blending of the inorganic pigment Y exhibiting a yellowish color) have nearly equivalent color tones, show nearly equal b* values, and have comparably high degrees of color tone stability. Comparative Examples 1, 8, and 9 corresponding to those Examples (having blended therein no inorganic pigment exhibiting a yellowish color) have nearly equivalent color tones, but have b* values of less than 10.0, and have poorer color tone stability as the blending amount of the polyaryletherketone resin increases, the color tone stability becoming poorer in the order of Comparative Examples 9, 1, and 8. This means that, when the b* value is less than 10.0, a larger blending amount of the polyaryletherketone resin leads to poorer color tone stability, and when the b* value is 10.0 or more, the color tone stability is comparably high irrespective of the blending amount of the polyaryletherketone resin, suggesting that, as the blending amount of the polyaryletherketone resin increases, the color tone stability-enhancing effect obtained by adjusting the b* value to 10.0 or more increases. The same applies to Examples 26, 33, and 34, in which the kind of the inorganic pigment exhibiting a yellowish color was changed.

In this connection, the test piece of Comparative Example 1 was subjected to the following test: in the evaluation of the color tone stability, a filter configured to block light having a wavelength in a specific region was used together with the UV filter in the xenon lamp to limit the wavelength of the light with which the test piece was to be irradiated. The results are shown in Table 3.

TABLE 3

| Irradiation wavelength | Color tone of irradiation light | Color tone stability ΔE* |
| --- | --- | --- |
| 410 nm to 550 nm | Blue light | 1.6 |
| 550 nm to 690 nm | Yellow light | 1.3 |
| 380 nm to 450 nm | Purple light | 5.3 |
| — | White light | 5.6 |

In the case of exposure to blue light or yellow light, a small color tone change was shown, and in the case of exposure to purple light, a large color tone change was shown. In view of this, it may be said that purple light makes a significant contribution to the color tone change of the polyaryletherketone resin material due to exposure to visible light. The results support the following effect of the present invention: the amount of purple light to be absorbed by the polyaryletherketone resin is decreased by imparting a color tone of the opposite color of purple, which ranges from yellowish green to yellow (yellowish colors), to the polyaryletherketone resin material, and thus the discoloration of the polyaryletherketone resin material due to exposure to light is suppressed.

The invention claimed is:

1. A polyaryletherketone resin material for dental use, comprising a polyaryletherketone resin and inorganic particles, and having a b* value of 10.0 or more in terms of colorimetric value of a 1.0 mm molded body in a CIELab color system under a black background condition,
wherein the inorganic particles include a brown inorganic pigment, and the brown inorganic pigment has a maximum absorption wavelength in a range of 490 nm to 560 nm in a measurement range of 360 nm to 830 nm.

2. The polyaryletherketone resin material for dental use according to claim 1, wherein the polyaryletherketone resin material for dental use has an L* value of 60.0 or more in terms of colorimetric value of the 1.0 mm molded body in the CIELab color system under the black background condition.

3. The polyaryletherketone resin material for dental use according to claim 1, wherein a blending amount of the polyaryletherketone resin is 40 parts by mass or more with respect to 100 parts by mass of the polyaryletherketone resin material for dental use.

4. A method of producing a resin composite material for dental use, comprising melt-kneading, at a temperature in a range of 340° C. to 500° C., a composition containing a polyaryletherketone resin and inorganic particles, the inorganic particle including a brown inorganic pigment, the brown inorganic pigment having a maximum absorption wavelength in a range of 490 nm to 560 nm in a measurement range of 360 nm to 830 nm.

5. The polyaryletherketone resin material for dental use according to claim 2, wherein a blending amount of the polyaryletherketone resin is 40 parts by mass or more with respect to 100 parts by mass of the polyaryletherketone resin material for dental use.

6. The polyaryletherketone resin material for dental use according to claim 1, wherein the brown inorganic pigment includes an oxide.

7. The method of producing the resin composite material for dental use according to claim 4, wherein the brown inorganic pigment includes an oxide.

* * * * *